(12) United States Patent
Fishkind et al.

(10) Patent No.: US 11,508,464 B1
(45) Date of Patent: Nov. 22, 2022

(54) TECHNOLOGY PLATFORM FOR CARE PLANNING AND COORDINATION

(71) Applicant: Hope Portal Services, Inc., Holmdel, NJ (US)

(72) Inventors: Joshua A. Fishkind, Red Bank, NJ (US); Michael Carnevale, Grand Rapids, MI (US)

(73) Assignee: HOPE PORTAL SERVICES, INC., Holmdel, NJ (US)

( * ) Notice: Subject to any disclaimer, the term of this patent is extended or adjusted under 35 U.S.C. 154(b) by 214 days.

(21) Appl. No.: 16/908,385

(22) Filed: Jun. 22, 2020

(51) Int. Cl.
*G06Q 40/00* (2012.01)
*G16H 10/20* (2018.01)
*G16H 40/20* (2018.01)
*G16H 10/60* (2018.01)

(52) U.S. Cl.
CPC ............. *G16H 10/20* (2018.01); *G16H 10/60* (2018.01); *G16H 40/20* (2018.01)

(58) Field of Classification Search
CPC ........ G06Q 40/00; G06Q 40/08; G16H 10/20; G16H 40/20; G16H 10/60
See application file for complete search history.

(56) References Cited

U.S. PATENT DOCUMENTS

| | | | |
|---|---|---|---|
| 6,430,542 B1* | 8/2002 | Moran | G06Q 40/06 705/36 R |
| 8,930,253 B1* | 1/2015 | Ball | G06Q 40/10 705/36 R |
| 2003/0182290 A1* | 9/2003 | Parker | G06Q 99/00 |
| 2016/0162992 A1* | 6/2016 | England | G06Q 40/06 705/36 R |
| 2019/0272915 A1* | 9/2019 | Tolbert | G16H 10/60 |

FOREIGN PATENT DOCUMENTS

WO   WO-0231707 A1 *  4/2002  ............. G06Q 10/10

OTHER PUBLICATIONS

An Introduction to Planning for People with Special Needs P McAvoy—Journal of Gift Planning, 2003—pgdc.com (Year: 2003).*

* cited by examiner

*Primary Examiner* — Lalita M Hamilton
(74) *Attorney, Agent, or Firm* — Eversheds Sutherland (US) LLP

(57) ABSTRACT

Platform for care coordination and planning. Integration of care planning tool, frontend applications, and customer support platform to assist in trust administration for beneficiaries who may have disabilities. The platform may be used to provide planning, concierge, and fiduciary services.

17 Claims, 11 Drawing Sheets

300

Requests

| Money | Medical | Food | Car | Online Services |

Care Plan (pie chart) $3,520
- $1025 Rent
- $800 Food
- $373 Transportation
- $1200 Utilities Contact Your Hope Care Coordinator
- Online Chat
- Email
- 1(800)321-1234
- Emergency Services Upcoming Service Requests

| Dentist Appointment | 500 Cherry St, Grand Rapids, MI 12345 | Mon, Sept. 14, 10:22am |
| Doctors Appointment | 1234 Common Ave., Madison, WI 12345 | Tue, Sept. 15, 07:56am |
| Grocery Delivery | Organic Grocers | Fri, Sept 30, 1:29pm |
| Taxi Cab – To Library | Hello Cab Company | Sun, Oct. 4, 3:56pm |
| Taxi Cab – To Library | Yellow Cab Company | Mon, Oct 5, 3:00pm |

Money Requests

| $38.00 | Shopping | New Book | 09/13/2018 |
| $79.00 | Entertainment | Tickets | 09/12/2018 |
| $1500.00 | Shopping | Bicycle | 09/02/2018 |
| $100.00 | Food | Holiday Party | 09/01/2018 |
| $230.00 | Travel | Trip to Toronto | 08/13/2018 |

- Home
- Finances
- Providers
- Care Plan
- Family/Friends
- Document Vault
- Activity Feed
- Settings
- Upgrade Plan
- Log Out Hello, Beneficiary Update Plan Questions? We're here to help

FIG. 3

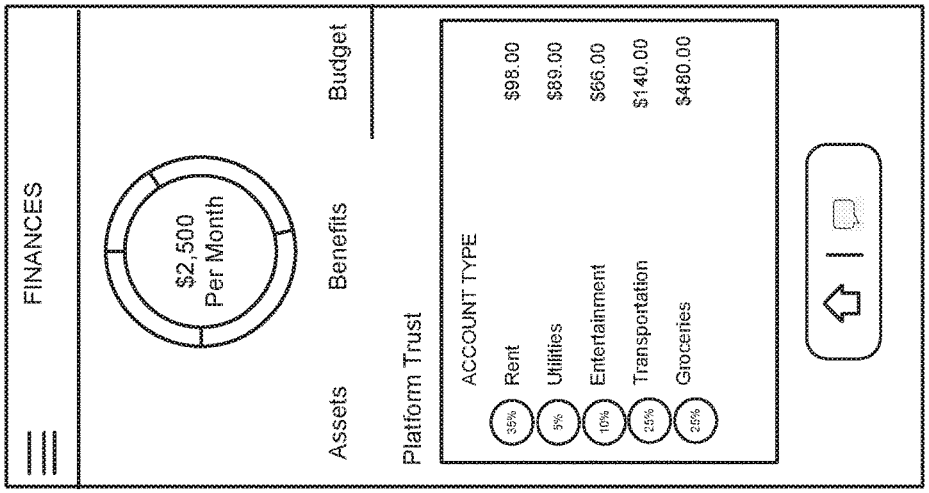
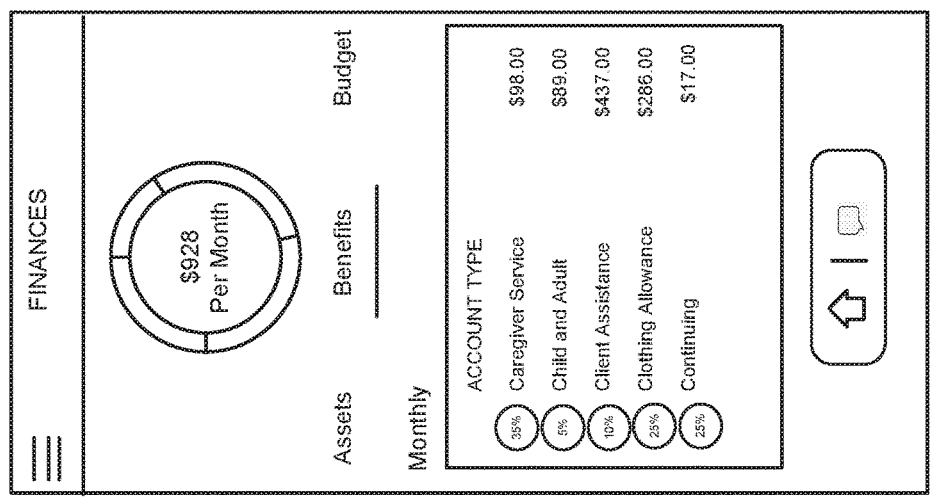
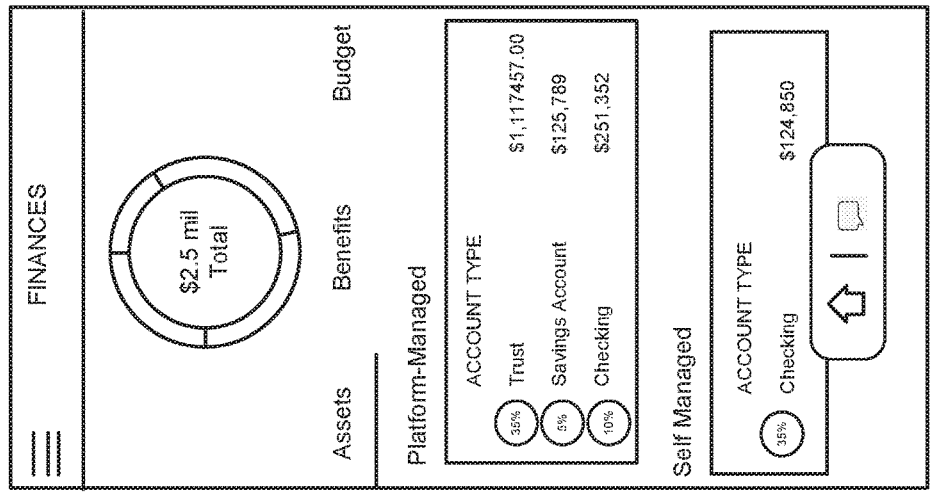
FIG. 6

Jason Alexander Wright

| | |
|---|---|
| Age | Email |
| 36 | jwright@photomail.com |
| Gender | Location |
| Male | Grand Rapids, Michigan |
| DOB | Major Challenges |
| 08/24/1979 | alcoholism, Asperger's, depression |
| Cell | |
| 1 (616) 260-9087 | |

- Beneficiary Accounts
- Approved Vendors
- Reports
- Forms
- Request
- Tickets
- Care Plan
- Harvest
- Settings
- Log Out Overview | Info | Finances | Account Users | Documents | Providers | Gov. Trust Doc Radar chart axes: Ability to Express Needs, Emotional Stability, Physical Ability, Financial Ability, Honesty/Trust Summary
Updated 03/21/2018

Plan Type: Active ▽   Plan Type: Manager ▽
Save

Create New Post — Post

You April 26, 2018
I've checked with your insurance company and received prior authorization for the drug you requested. Your doctor will be updated You April 25, 2018
Yesterday I went to the doctor to get an injection for my knee. The doctor was unable to give me the injection because he said my insurance company said I was not authorized. Can you help me with this?

TECHNOLOGY PLATFORM FOR CARE PLANNING AND COORDINATION

BACKGROUND OF THE INVENTION

Millions of individuals across the country suffer from various types of disabilities including developmental disorders (e.g., autism), mental disorders (e.g., schizophrenia), and physical disabilities (e.g., blindness). These individuals, their parents or their caretakers, all need some form of help in creating a plan to protect their finances, health care benefits and essential services. They need a financial safety net around them, including estate planning, retirement planning, financial planning, life insurance planning, government benefits programming, and integrating these efforts with protocols established by a clinical care team. Unfortunately, these disciplines have, heretofore, acted autonomously, siloed from each other's opinions, and fragmented, leaving the disabled beneficiary at risk. The proverbial right hand does know what the left hand is doing.

In most cases, a special needs trust is essential to protect the beneficiary. The trustee may be empowered to distribute funds from the trust for the beneficiary's benefit. But what if the trustee does not really know the beneficiary? For example, Bank Trustees often never meet the beneficiary and know nothing of their medical history, nuances, or other resources. Too often the Trustee doesn't know how much money is in a beneficiary's account, and therefore is unaware that a distribution could violate key government benefits regulations such as Medicaid eligibility. The absence of such data prevents the Trustee from prudently exercising its discretion, creating risk for both the Trustee and Beneficiary each time a distribution is made.

The consequences of not knowing the beneficiary and not having the requisite data are high, both to the professionals, and more importantly, to the millions of disabled beneficiaries who may be relying on SSI benefits or Medicaid for crucial services or income. The Courts have recently had exposure to these exact problems, resulting in trustees being fined, censured or terminated. In some cases, the beneficiary's benefits were terminated, or they never received any funds from the Trustee, leaving an already vulnerable individual at greater risk. At its core, the problem is that the requisite data has not been stored, collected, or analyzed to provide the trustee with the very information it requires to prudently exercise its discretion.

The instant application solves these issues with a first of its kind technology platform that: 1. enables parents, caretakers or guardians to design a life care plan which incorporates the team of advisors and enables integration of skill sets; 2. quantifies the amount of funds required to fund the plan using the Meet Your Trust Objectives (MYTO) tool; 3. drafts a trust agreement tailored to the individual's needs, and; 4. empowers a trustee to prudently and efficiently discharge it's duties based on clearly established parameters.

BRIEF DESCRIPTION OF THE DRAWINGS

Various techniques will be described with reference to the drawings, in which:

FIG. 3 illustrates a beneficiary dashboard, in accordance with at least one embodiment;

FIG. 6 illustrates a finances dashboard implemented in the context of a mobile application, in accordance with at least one embodiment;

FIG. 7 illustrates a detailed view of a beneficiary account from the perspective of a care coordinator, in accordance with at least one embodiment;

DETAILED DESCRIPTION OF THE INVENTION

As described in greater detail below, at least one embodiment of the present invention is a first-of-its-kind planning tool leveraging medical, behavioral, and psychological health that can be used to improve trust administration for persons with disabilities (e.g., autism), resulting in better quality-of-life and/or other health-related outcomes. The health planning tool may refer to a computer-based service platform that is utilized by multiple parties—including but not limited to grantors, beneficiaries, trustees, care coordinators, medical professionals and/or organizations, legal professionals and/or organizations, financial professionals and/or organizations, and more—to provide planning, concierge, and fiduciary services.

Figure 1:
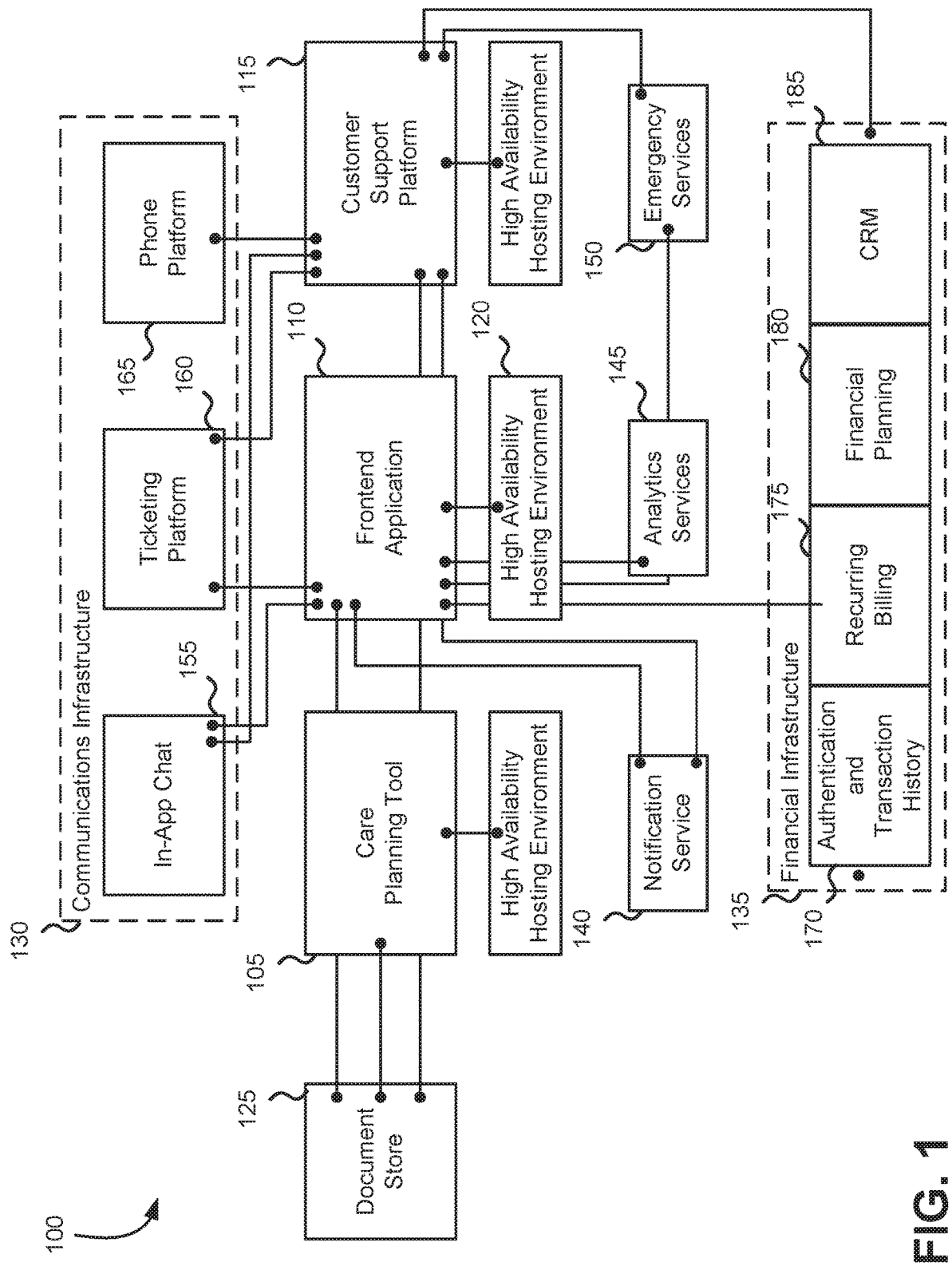
FIG. 1 illustrates a computing environment in which various embodiments may be implemented.

FIG. 1 illustrates a computing environment 100, in accordance with at least one embodiment. The computing environment 100 may implement a service platform to provide planning, concierge, and fiduciary services. A care planning tool, as illustrated in FIG. 1, may include a care planning tool 105, a frontend application 110, and a customer support platform 115 that serve as the center pieces of a service platform for providing planning, concierge, and fiduciary services, as described in greater detail hereinbelow. A care planning tool, in at least one embodiment, runs on a highly available hosting environment 120 such as a cloud service provider that can facilitate collection of data about a beneficiary and crafting of a care plan which sets the parameters for trust administration. The high availability hosting environment 120 may provide computing services such as virtual machines, servers, and other computing resources that may be used to run software for the care planning tool. Data may be collected when a grantor registers with the service platform, in the form of one or more questionnaires, which are used to generate an initial care plan. Over time, data may be continuously collected from various sources, such as from periodic appointments, and that data may be used to update the care plan to adapt the parameters based on the evolving needs of the beneficiary. In some cases, the beneficiary may exhibit a greater need for certain services, but in other cases, services may no longer be needed, or a reduction may be appropriate. The care plan and corresponding collected data may be stored and referenced in a document store 125.

The document store 125 may be hosted on a cloud service provider which may be the same or different service provider as that which provides the high availability hosting environment 120. The document store 125 may securely store documents, files, databases, emails, chat histories, and other digital data which is generated and/or utilized by the service platform. The data may be natively encrypted to protect the privacy and security of the data. In some cases, data may be stored according to regulations and laws that govern the storage of such data, for example in the case of medical data which may be subject to HIPAA guidelines and retention policies. The document store 125 may also be accessible to the frontend application 110 and/or the customer support platform 115.

The frontend application 110 may refer to various technologies which a user can use to access the care planning tool and different services provided therein. In many cases, the frontend application 110 supports both a web application that the user can access using traditional computer systems, as well as a mobile application which is particularly suited for mobile devices but may also be used with other types of computing devices. In various embodiments, a user may download a mobile application to his or her smartphone and either register or login to the frontend using existing credentials. Once the mobile application is loaded and credentials have been verified, the user may have access to various planning, concierge, and fiduciary services which are backed by the computing environment 100 illustrated in FIG. 1. The frontend application 110 may be used by the user to make requests for money or in-kind services, such as making medical appointments, scheduling care worker visits, scheduling grocery deliveries, scheduling calls with financial and/or legal advisors, and any other such service that may be within the parameters of the care plan for a particular beneficiary. The frontend application 110 may be connected to the document store 125, communications infrastructure 130 (or a portion thereof), financial infrastructure 135 (or a portion thereof), customer support platform 115, notification services 140, analytic services 145, and emergency services 150. The communications infrastructure 130 may include an in-app chat applet 155, a ticketing request platform 160, and a phone platform 165 that can be used to facilitate communications between the end user and care coordinators using the customer support platform. The in-app chat applet 155 may be embedded in a website application that allows the user to immediately start communicating with a care coordinator in real time. A phone platform 165 may be used to route phone calls to care coordinators which are able to speak with users directly to facilitate requests, which may subsequently be entered into the ticketing platform 160 by a care coordinator on behalf of a grantor or beneficiary that is not able to do so over on a computer, which may be due to a disability or a preference to avoid using computers. The phone platform 165 may be a call center support hub that supports multiple care coordinators taking calls from multiple customers and may support call recording. Requests submitted by grantors, beneficiaries, and others may be routed to the ticketing platform 160 that can generate a ticket for each request, and those requests are accessed and processed by care coordinators either in real-time or later, based on the nature and urgency of the request.

The ticketing platform 160 may include queues for different types of requests and may, in some cases, aggregate requests by location. For example, if there are multiple requests for grocery deliveries within a particular neighborhood or geolocation, those requests may be aggregated based on requested time (e.g., same day) and location (e.g., same neighborhood) and processed together. Therefore, a grocery delivery provider may be able to make more efficient trips to satisfy the multiple requests.

A user's applications may also be connected to a notification service 140 which may be implemented using a highly available hosting environment such as those used elsewhere in FIG. 1 (e.g., environment 120). The notification service 140 may be used to update the user on the status of pending requests, such as when a service has been scheduled or when money requested for particular needs has been reviewed, approved, and disbursed. The notification service 140 may be used to push notifications to users reminding them of upcoming appointments, overdue services, and other important information. For example, a notification service 140 may push a notification to the user's mobile app notifying them that an upcoming grocery delivery is running behind schedule and may be late. As a second example, a notification service 140 may send a text message to a beneficiary the day before a doctor's appointment, reminding him that transportations services are scheduled to bring him or her to the doctor's office at a particular time. As yet another example, a notification service 140 may call a beneficiary if he or she has yet to see a social worker based on parameters set forth in the care plan (e.g., missed a bi-weekly visit schedule).

Emergency services 150 may be connected to the frontend app location 110 as well as the customer support platform 115 in case of emergencies. Either the client or care coordinator can use the emergency services 150 to notify police or medical personnel of the user's location, name, and nature of emergency. In some cases, the user may initiate an emergency services request via the web or mobile app which is routed to a care coordinator. If the user is subsequently unresponsive, the care coordinator may use emergency services and notify police and/or medical personnel of the user's location and what the nature of the emergency might be.

An analytics service 145 can track and report web and/or app traffic. The analytics data may be stored, aggregated, analyzed, and reported to determine how the product is being used by customers and identifying usage patterns which can be used to generate insights into, for example, the usage pattern of web application users vs. mobile application users.

The customer support platform 115 may be used by care coordinators to communicate with users and coordinate various planning, concierge, and fiduciary services. As discussed above, users can contact care coordinators via the communications infrastructure to schedule appointments, request in-kind and monetary benefits, and the like. When a request ticket is created, a care coordinator may receive a notification and have the opportunity to review the request. In some cases, the requests may be denied if they are outside the parameters of a care plan. For example, if a care plan relies on certain government benefits such as Social Security Disability Insurance (SSDI) or Supplemental Security Income (SSI), requests for disbursements that would make the beneficiary ineligible for such benefits may be denied. Accordingly, the customer support platform 115 may be integrated with financial infrastructure 135 that includes financial account information which is surfaced to care coordinators which can be used as part of reviewing some or all request tickets. The financial infrastructure 135 may include authentication and transaction history 170, recurring billing 175, financial planning 180, and CRM components 185. The authentication and transaction history component 170 may be implemented at least in part by an external service such as PLAID™ which connects with users' bank accounts to access transaction information and validate account ownership, and more. The recurring billing 175 may be implemented at least in part using an external service such as STRIPE™ which implements payment processing APIs which can be used to pay bills on behalf of a customer. The financial planning component 180 may be a third-party financial planning software solution such as ADVICENT™ but may also be an internal software solution which may, at any point in time, be used in place of the third-party solution. Finally, a client relationship management (CRM) system 185 such as ZENDESK SELL™ may be utilized as part of the financial infrastructure to deliver financial information to the customer support platform.

Meet Your Trust Objective Planning Tool

In some cases, the financial planning component 180 can include the Meet Your Trust Objective (MYTO) planning tool. The MYTO planning tool can receive various financial and demographic information of a user and of a potential trust beneficiary to determine criteria and parameters for funding a trust. The MYTO planning tool can in some cases be implemented into a care plan generation discussed in more detail below. Further, in some cases the MYTO planning tool can implement decision logic features (e.g., removing and/or swapping questions based on previously answered questions) discussed in more detail below.

Figure 11:
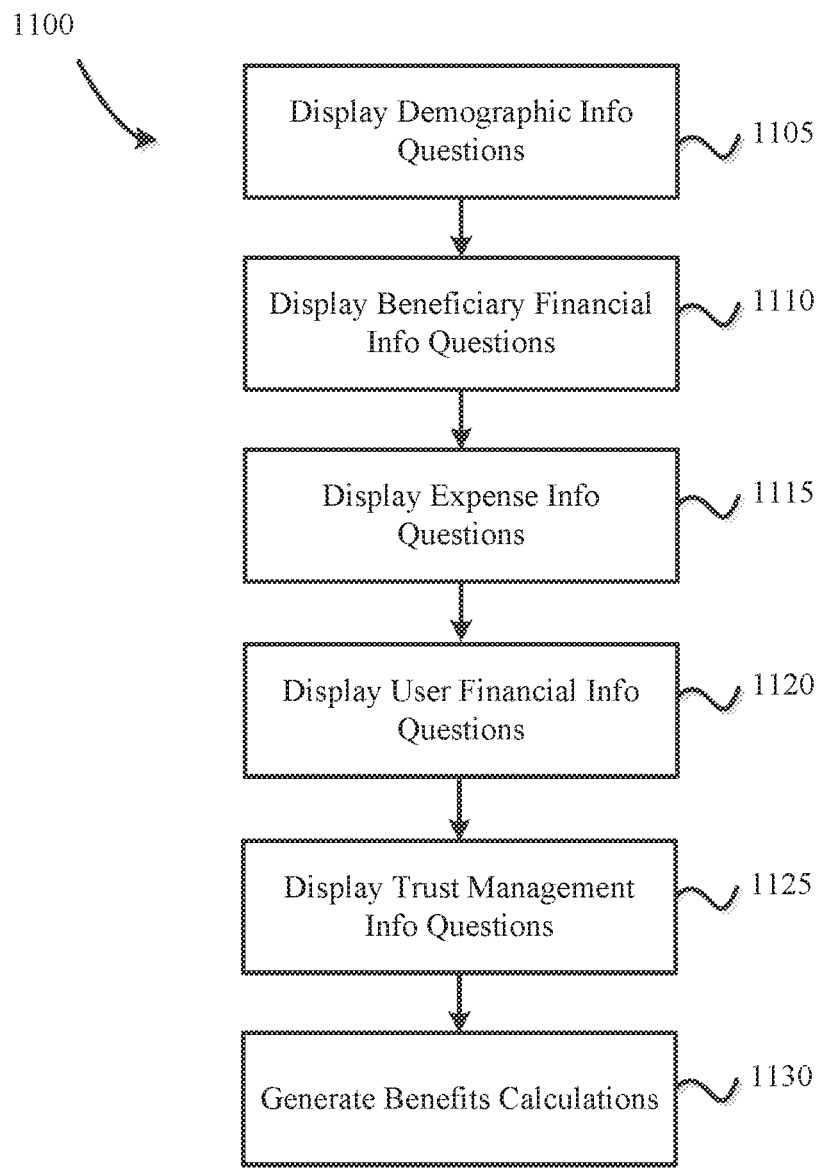
FIG. 11 shows an illustrative example of a process to generate benefits calculations in accordance with at least one embodiment.

FIG. 11 depicts a workflow process 1100 for calculating trust financial values according to an embodiment of the present invention. A user may be displayed 1105 a series of questions pertaining to demographic information of the user. For example, the user can be requested to answer questions pertaining to name, age, gender, marriage status, spouse demographic information, dependent demographic information, and the like.

The user may then be displayed 1110 a series of questions pertaining to financial information of the potential beneficiary of a trust. For example, the user can be requested to answer questions pertaining to financial benefits received by the beneficiary (e.g., Social Security, SSI, Medicaid, Medicare, and the like).

The user may then be displayed 1115 a series of questions pertaining to expense information of the potential beneficiary. For example, the user may be requested to answer questions pertaining to monthly or annual housing expenses, food expense, utility expenses, health care expenses, transportation expenses, insurance expenses, and the like. In some cases, the expense questions can be more granular in nature. For example, under housing expense categories, the user can be displayed questions pertaining to monthly or annual mortgage costs, rental costs, property tax costs, and the like.

The user may then be displayed 1120 a series of questions pertaining to financial assets of the user. For example, the user may be requested to answer questions pertaining to home value, retirement account values, special asset values, business interest values, and the like.

The user may then be displayed 1125 a series of questions pertaining to trust management for the potential trust. For example, the user may be requested to answer questions pertaining to the annual cost of managing the trust (e.g., a trustee's fee percentage), a portfolio risk weighting (e.g., a percentage of the portfolio to be held in stocks), a desired fund life (e.g., in years to match the beneficiary's life expectancy), and the like.

From the received answers, the planning tool can generate 1130 benefits calculations corresponding to the potential trust. For example, the planning tool can calculate total required principal values for the trust, total required principal values without benefits, current annual and lifetime benefit values. These values can be displayed to the user and/or stored (e.g., in local or cloud memory) for future use.

Web Application

A user, as described elsewhere in this disclosure, may refer to any suitable individual or organization that can access the service platform and may include, without limitation, beneficiaries of a trust, grantors, trustees, trusted family members which are granted full or partial permissions, and many other such individuals. Organizations may be users as well, for example, an organization or an agent acting on behalf of an organization may be a user of the service platform to access information relating to a beneficiary that the organization is a trust administrator for.

In many cases, a user may be prompted to provide information as part of a registration process for using the service platform. For example, consider the case in which a user is setting up a trust for a beneficiary with special needs (e.g., autism). The user may be prompted to provide information about who the account is being established for and additional information about the beneficiary may be requested, such as name, address, birthdate, social security number or other government identification information, email, phone number, and the like. A photo of the beneficiary may also be requested. Continuing the example, the user may be required to describe his or her relationship with the beneficiary. For example, the user may be the parent of the beneficiary or a legal guardian. The user may be another family member or a friend. The user may be an agent of an organization that was appointed as a trustee over a trust which is to be administered for the benefit of an individual. Other relationships are possible, and the examples provided above shall not be construed to be limitative as to the types of relationships which can exist between the user and the beneficiary.

The benefactor may be prompted to provide information about himself or herself, which may be the same as or different from the fields discussed above in connection with the beneficiary. Upon providing at least a portion of the requested information, the registration process may be complete, and the user may be registered with the service platform. In some cases, a user can be a beneficiary of a trust, a trust administrator, a third-party to the trust, and others, Registered users may have various avenues available to access the service platform, which may include a website, mobile application, or various other electronics-based graphical user interfaces. As described in greater detail below, a graphical user interface can be used by a beneficiary to access and view the details of the trust. In some cases, the graphical user interface can include an introductory splash screen that gives new users a tour of the various features of the service platform and where to begin the trust process.

Figure 2:
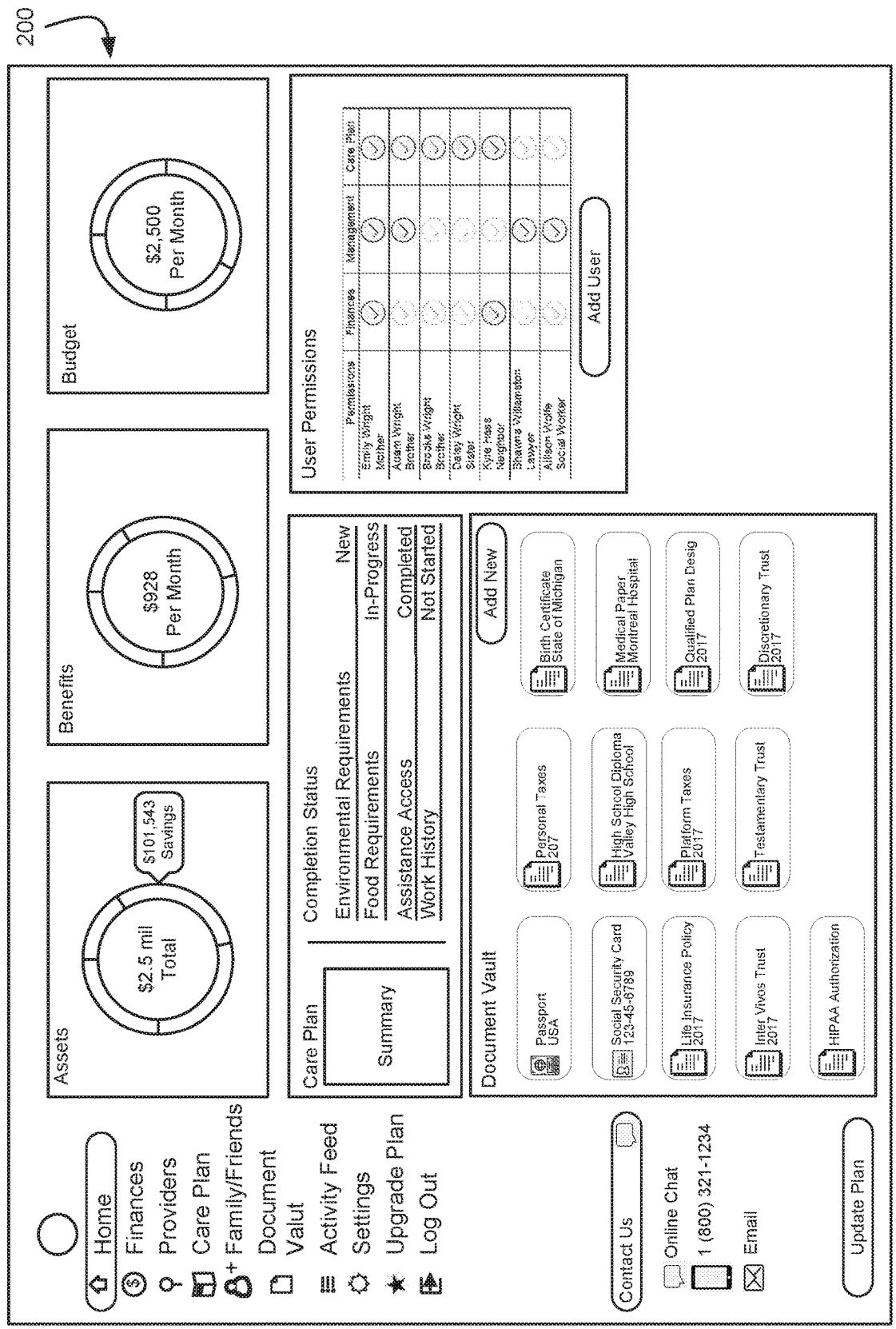
FIG. 2 illustrates a grantor dashboard, in accordance with at least one embodiment.

In accordance with at least one embodiment, FIG. 2 illustrates a grantor dashboard GUI 200 which may be the landing page for the service platform website. The graphical user interface may include a menu list located for convenient access, such as along the left side of the screen. The menu list may include embedded links that can be used to surface different aspects of a trust, such as finances; providers; care plan; users (e.g., family and friends); document vault; activity feed; settings; and more. Clicking on any of these may bring the user to a new page that surfaces the requested information in greater detail.

The grantor dashboard GUI's landing page may be a home screen that includes an overview of various aspects of the trust. The grantor dashboard GUI may include a combination of graphical and textual data that reflects a past, current, and/or anticipated state of assets, benefits, and budget. For example, an Assets graph may be presented as a pie graph, bar graph, line graph of assets over time, etc. The total current value of assets may be surfaced as text in or around the Assets graphs. In some cases, information relating to the Assets graph is presented when the user highlights or touches an area at or around the Assets graph. For example, the Assets graph may be a pie chart that is divided into the different sources of assets which may be color coded, and when the user's mouse cursor hovers over a particular color coded section of the chart, the value of that particular asset source may be displayed, and when the user's mouse cursor moves to another part of the GUI, the information relating to the asset source may disappear from the screen.

Likewise, a Benefits graph may be presented in the same or similar fashion, subdivided by the types of benefits being received (e.g., social security disability and supplemental security income) and aggregating the actual or expected benefits received on a monthly or annual basis. The calculation of monthly benefits can be done on a rolling N-month basis, month-by-month basis, or any other suitable calculation for estimated or actual benefits. Projected benefits may be calculated based on an enumerated list of recurring or periodic benefits which may include the trust assets, government assistance, and other sources. Similarly, a Budget graph may be represented, like the Benefits graph, of expected and/or actual monthly expenditures on a monthly or annual basis.

For some users, the grantor dashboard GUI can include a user permissions panel that displays a list of user permissions. This aspect of the grantor dashboard GUI may show specifically to users which are granted management permissions (as described in greater detail below). The user permissions on the grantor dashboard GUI may display some or all users associated with a trust and a corresponding set of permissions for each of those users. The users may be presented in the GUI with additional information, such as a relation with the beneficiary (e.g., family, friend, professional) and/or whether the user is an emergency contact for the beneficiary. For example, a close family may be entrusted with permissions to view and/or manage finances, management, a care plan, and more. The grantor dashboard GUI may be read-only, in the sense that the user permissions can be viewed but not modified from the grantor dashboard GUI—a link to modify user permissions may be included in the user permissions panel and/or the menu list displayed elsewhere in the grantor dashboard GUI. The user permissions panel may be hidden from users that lack management permissions for the trust account.

The grantor dashboard GUI may further include a document vault panel that displays a list of documents accessible to the present user. The document vault panel may display an organized list of icons that represent digital documents stored in a document vault. Files stores in the document vault may be encrypted and stored on a data storage service such as AMAZON S3™ and BOX™. The document vault may include digital copies of various types of legal documents, financial documents, medical documents, government documents, testamentary documents, and more. In some cases, the digital documents are authenticated digital copies. In some cases, the documents are digital copies of physical documents, such as an image or scan of a birth certificate. The document vault may include a care plan setting out parameters to provide planning, concierge, and fiduciary services. In some cases, not all documents of the document vault are available to a user—for example, a user that has permissions for financial information but not medical information may have access to bank and investment statements in the document vault, but that user may simultaneously lack access to the user's birth certificate, HIPAA authorization, and other medical-related documents which may be stored in the document vault for the user. The following examples of documents which may be stored in the document vault in digital form are to be construed as non-limiting and are merely illustrative as examples of types of documents that can be stored within the document vault: passport information; tax returns; birth certificate; social security card; educational diplomas and/or transcripts; cognitive assessment; life insurance policy; qualified plan beneficiary designation; trust documents; and authorization forms such as HIPAA authorization and power of attorney documents. Documents described herein may be signed, digitally signed, authenticated (e.g., sealed), witnessed (including signatures thereof), notarized, or any combination thereof. The document vault panel may include a button to add more documents where the user can select a locally stored document to upload to the document vault, which can be stored by the service platform so that other users can access the data and/or for archiving.

A grantor dashboard GUI may also include a completion status panel that includes the completion status for various items in the care plan. A user can click into any section to begin or continue answering questions for the selected section. The completion status may be organized into separate sections that relate to different aspects of a trustee's life, including environmental requirements—for example, whether a physical disability hinders the day-to-day activities of the trustee—food requirements, assistance areas, work history, and more.

FIG. 3 illustrates a beneficiary dashboard GUI 300, in accordance with at least one embodiment. The beneficiary dashboard may be the landing page for a beneficiary user when he or she logs into the service platform. The beneficiary dashboard may incorporate elements of the grantor dashboard, such as a menu list, but the entries in the menu list may be different or the same. The menu list may include items to navigate to, such as finances, providers; care plan; family and friends; document vault; activity feed; settings; and more.

The beneficiary dashboard may include a Requests panel that provides the user quick access to different types of requests such as requests for money (e.g., cash disbursements), medical, food, transportation, and other in-kind services. When a beneficiary clicks on an icon for money, he or she may be prompted to enter how much money he or she is requesting and then what the reason is for the request. The money request may then be routed to a care coordinator who reviews the request in view of the care plan parameters and the user's profile information to determine whether the request should be granted. For example, a user exhibiting low trustworthiness score may have requests for money scrutinized more closely. A request for medical services may first prompt the user to type in why he or she would like to see a doctor and then which doctor he or she would like to see. A list of medical providers (e.g., filtered based on the user's provided reason) may be included to provide suggestions to the user, or the user may select a new doctor, or the user may select an option to allow the care coordinator to select the best suited doctor given the provided request description. Finally, the user may be prompted to select a preferred time to see the doctor. The user may be prompted to select a first, second, and third choice times, which can be used to help with scheduling in case of conflicts.

The beneficiary dashboard may include a Budget panel which may be similar to the budget panel described above. The Budget panel may include a pie chart of an actual or expected budget, including a total monthly budget as well as breakdowns of the largest budget items, such as rent, food, transportation, utilizes, etc. and their respective amounts.

A Contact panel may include one or more methods by which the user can contact a care coordinator. For example, there may be an "online chat" option that pops up a chat window or navigates to a chat window which the beneficiary can use to contact a care coordinator, submit requests, ask questions, schedule appointments, and more. Other options for contacting a care coordinator may include using email, telephone calls, and more. Additionally, the Contact panel may include an "Emergency Services" option that may be displayed differently or more prominently than others. The "Emergency Services" option can be used to contact emergency services. In some cases pushing the button prompts the user for the nature of their emergency and either the user or a care coordinator will be routed to a call (e.g., voice-over IP call) to police, hospital, or other emergency services based on the nature of the emergency, as indicated by the user. In some cases, the option to perform an online chat with a care coordinator is present throughout different pages via a floating help button that is presented in the lower-right corner of the screen and persists even as the user scrolls through the screen—hence "floating."

The beneficiary dashboard may include an Upcoming Services Request panel that includes a list of scheduled appointments or services. For example, the panel may include upcoming dental appointments, physical therapy sessions, social worker visits, grocery deliveries, and transportation (e.g., taxi rides) schedule. The panel may include additional information such as a location for an upcoming event and the event time. In some cases, the panel also includes overdue events—for example, if a social worker visit is to be conducted every two weeks based on beneficiary needs and spelled out in the care plan, this panel may include a reminder to schedule a social worker visit or may prompt a care coordinator to reach out to the beneficiary to schedule the social worker visit at a time that is convenient for the beneficiary. The entries in the Upcoming Services Request panel may include entries that are setup and entered into the list by a care coordinator and may further include entries that are automatically generated based on parameters of a care plan.

While upcoming service requests reflect the delivery of in-kind benefits, pecuniary benefits may be surfaced in a separate Money Requests panel. The Money Requests panel may include a list of open, pending, and closed requests. A beneficiary may make requests for cash distributions via the Requests panel and those requests are surfaced in the Money Request panel. In at least some embodiments, when a money request is initiated, it is added to a queue of requests and starts in an "Open" state, indicating that the request is currently open and has not yet been evaluated. A request may transition from an "Open" state to a "Pending" state when a care coordinator reviews a request. In some cases, a request may include additional information or review, after which it may be finally approved or denied. If a request is approved, it may move into a "Processing" state while funds are being transitioned and then a "Closed" state when the funds are distributed. The Money Requests panel may include the status of requests, when the requests were made, the amount being requested, and what the funds were requested for. Users may be able to view money requests which have been processed and attach a receipt which is uploaded and stored on a backend server.

Figure 4:
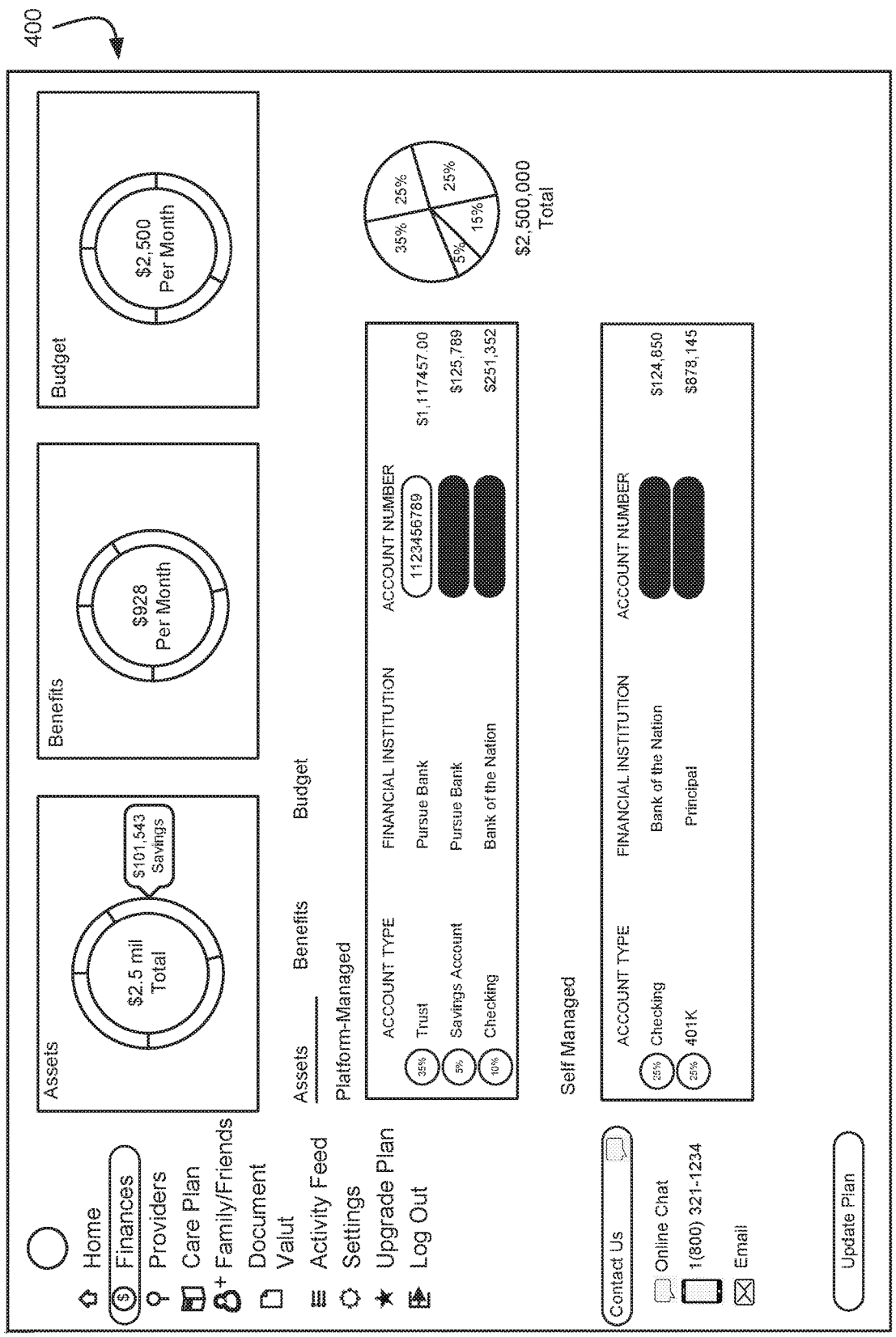
FIG. 4 illustrates a finances dashboard, in accordance with at least one embodiment.

FIG. 4 illustrates a finances dashboard 400, in accordance with at least one embodiment. The finances dashboard may be accessed by any permissioned user, for example, via a menu list on the user's landing page. The Finances dashboard may include more detailed information on assets, benefits, and budget which may be displayed—albeit at a higher level of generality—in the landing page. For example, the Finances dashboard may include the same Assets graph, Benefits graph, and Budget graph as described in connection with the grantor and/or beneficiary dashboard. Information presented on the finances dashboard may be organized according to the whether it is related to assets, benefits, or budget. For example, assets information may be shown under an "Assets" tab which can be switched by the click of a button to a "Benefits" tab or "Budget" tab based on what the user is interested in seeing.

The "Assets" tab may include a breakdown of assets available for use, which may include, for example, a trust corpus, savings and checking accounts, investment accounts, and more. Assets may be divided based on whether they are managed directly by or on behalf of the service platform or by other entities, such as the beneficiary. For example, the service platform may include assets that include a trust corpus which may be invested. In addition, the financial institution and account/routing numbers may also be accessible to the user. In some cases, the account and/or routing number may be hidden by default and only made visible when the user clicks on it or performs another action indicating that it should be visible, as a security precaution. The financial asset data may be obtained in connection with web service application programming interface (API) communications with third parties such as banking institutions and brokerages.

The "Benefits" tab may include a breakdown of benefits that the beneficiary is expected to receive. For example, benefits may include caregiving services, food services, assistance programs, allowances for clothing, and continuing education endowment, as non-limiting examples. A breakdown of the monthly benefits may be made on a rolling basis. The benefits data may be manually entered by a care coordinator. Likewise, the "Budget" tab may include monthly budgeting information, such as an allocation for rent, utilities, entertainment, transportation, groceries, and other costs incurred by the beneficiary.

An activity feed dashboard may be accessible via a menu list. The activity feed may include various sources of information relating to a user's care. For a user, the activity feed may include communications between the user and care coordinators. For example, a benefactor may initiate a chat with care coordinator with a request to setup daily grocery deliveries for a beneficiary. The activity feed may record this request and include a treed structure in which replies to the request are nested under the initial request. The activity feed may include a list of requests and ongoing conversations between care coordinators and users. Requests may be marked as having been completed by a check mark and/or greying out the conversation. The activity feed may also include other activities such as scheduling of upcoming appointments, upcoming activities, and more. The activity feed may be organized by latest reply, active requests, and more. The activity feed may be filtered so that only activities of a specific type are displayed.

A providers dashboard may include medical and/or service provider tabs. In this context, a medical provider may include specific doctors providing care to the beneficiary and may also include hospitals and health care facilities. The providers listed may be the preferred providers of the user and may include additional information such as specialty (where applicable) network (e.g., for health insurance), and location information. Medical provider and contact details may be read-only. If a user wishes to modify the medical provider information (e.g., add or remove a doctor, update office location) the user may be able to do so by contacting a care coordinator. The service provider tab may include information for non-medical related services which are available to a beneficiary. Examples of such services include home maintenance and cleaning services, food and grocery delivery, catering, and more. The services provider tab may include a list of businesses, a description of the services provided, contact information such as a phone number or website, office location, and more. The list may be read-only and can be updated by a care coordinator—for example, in response to a request for services that are fulfilled by a particular business.

A care plan dashboard may be a page in which a user can view, download, and share a care plan. The care plan dashboard may display icons for different questionnaire categories that profile different aspects of a user's needs. For example, the care plan may include separate questionnaires that focus on different aspects of the beneficiary's life: budget requirements, assistance area, food requirements, work history, mobility, finances, abilities, social, and physical fitness. Each questionnaire may focus on a specific aspect of the beneficiary's life that provides information which can be used to determine parameters for a care plan. When a beneficiary registers on the service platform, he or she may be prompted to complete each of the questionnaires but doing so at registration may be optional. At a later point in time, the beneficiary may navigate to the care plan dashboard to complete any unfinished questionnaires.

Each questionnaire may include a status indicator that shows the user whether a questionnaire has not yet been started, is partially completed, or fully completed. A questionnaire may include a series of questions organized as a decision tree in which an answer to a first question is used to select a second question from among a plurality of questions to present in sequence after the first question. A question may be presented as a binary question where the user selects between two possible choices (YES/NO, TRUE/FALSE, etc.), between multiple choices (e.g., selecting on a scale of 1-10 how much a user agrees with a statement), a numeric answer, an open-ended text box, and more. For example, under a finance-related questionnaire, a sample question may be a multiple-choice question asking how well the user is able to manage his or her own finances on a scale of 1-10. As a second example, a benefactor may be asked to describe how the beneficiary usually feels when he or she wakes up in the morning from a scale of 1-5, with a 1 being represented as a very unhappy face, and additional cartoon faces illustrates progressively happier faces corresponding with higher number values.

A family and friends dashboard may illustrate information relating to users who may have various levels of access. As described in connection with the grantor dashboard, a grantor or benefactor may have access to permission information for various users. For example, family members of the beneficiary may have access to management and care plan information and may be listed as emergency contacts. As a second example a lawyer may be listed as another user who has access to legal information stored in the document vault. The family and friends dashboard may include more detailed information on each user, such as their full name, birth date, address, email, phone number, and relationship with the benefactor. In some cases, the fields may be empty where not needed, such as birthday information for the benefactor's lawyer. The family and friends panel may also include buttons that allow a grantor to edit the permissions for different users. In at least some cases, adjusting permission settings is done on a by-request basis and requires approval by a care coordinator before the requested changes are applied. In some cases, users that do not have account management permissions do not see information for other users in the family and friends dashboard.

Mobile Application

Some or all of the functionality described above may be implemented in connection with a mobile application, in accordance with at least one embodiment. Mobile applications may refer to software running on a mobile device such as a smartphone, tablet, smart watch, or other suitable embedded device. These devices may be characterized has having significantly smaller screens than traditional GUIs on computers and laptops and may furthermore be characterized by using touchscreens as the preferred (or even only) form of human interfacing. The combination of a small screen and a touchscreen interface may result in particular challenges—especially for users with motor or physical disabilities—involved in implementing various features described above in the context of a mobile device.

Figure 5:
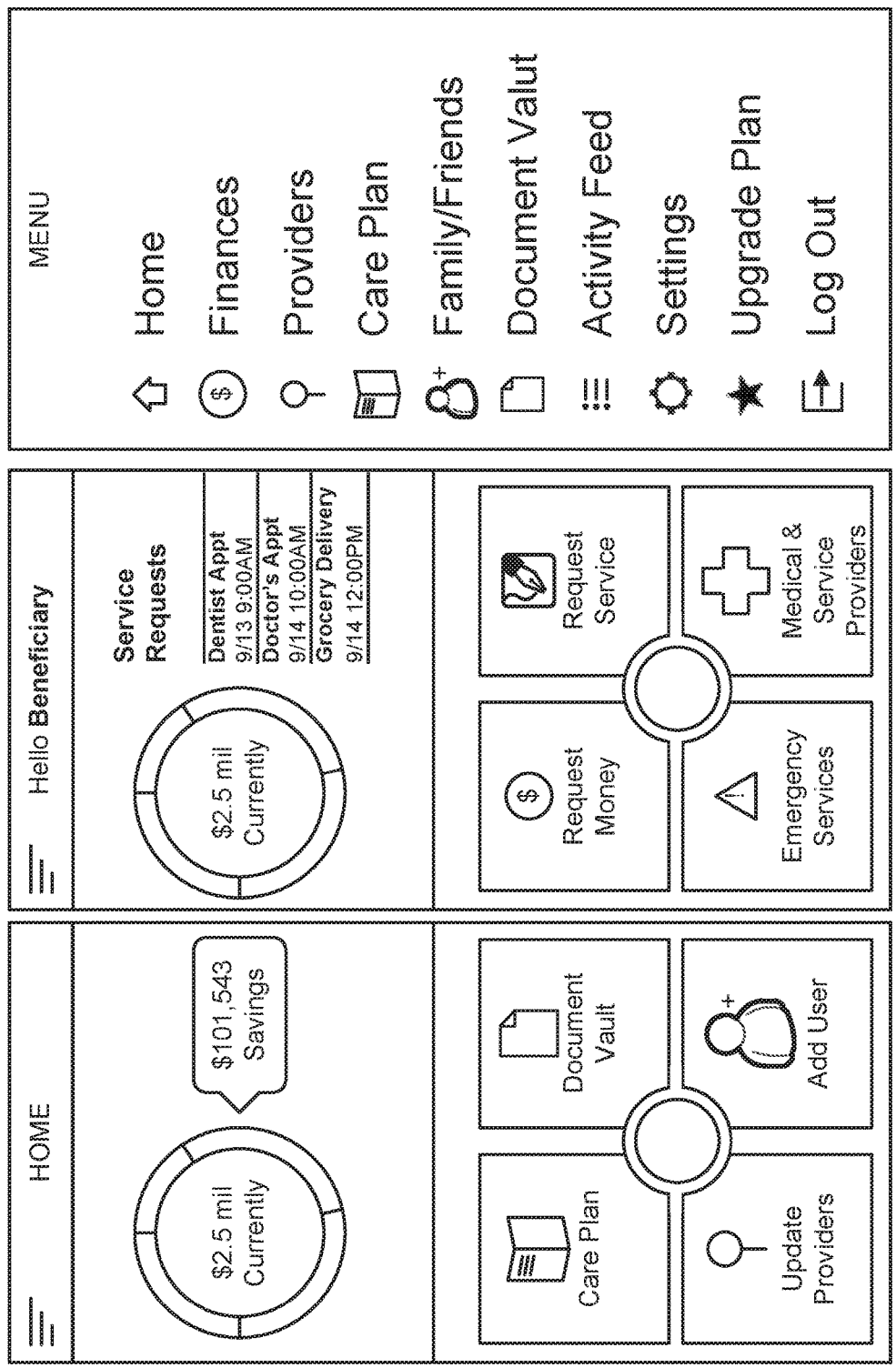
FIG. 5 illustrates a user dashboard implemented in the context of a mobile application, in accordance with at least one embodiment.

FIG. 5 illustrates a grantor dashboard 500, in accordance with at least one embodiment. The grantor dashboard may be implemented in the context of a mobile application, which as described above, may be particularly suited for use on a smartphone or other handheld device with a small screen and human touch interface.

Traditionally, computer users are limited in the ways in which they can organize icons on their display. Additionally, computer users may have a large number of icons on their display, making it difficult to find the icons most used. The typically available ways to organize icons are alphabetically, by file size, and by file type. If a computer user wants a non-typical arrangement of icons, the user would need to manually manipulate the icons on their display. For example, traditional software does not automatically organize icons so that the most used icons are located near the "start" or "home" icon, where they can be easily accessed. In the context of a mobile device with a small screen, it may be impossible for the mobile device user to organize the icons such that all icons are simultaneously visible on the screen at the same time. In fact, in many cases, only a small number of icons can be presented on the screen at a time due to size constraints on the icons—if the icons are too small, they will be difficult for users to tap, thereby making the mobile device less accurate and more frustrating for the user to operate. Therefore, what is needed is a method that allows for such non-traditional arrangements to be performed automatically. Therefore, what is needed is a method for selecting the most important icons to include on the screen such that the icons are both simultaneously accessible using human touch interfaces and enough icons are displayed so that the most commonly used icons are still easily accessible to the user.

Accordingly, at least one embodiment addresses this issue by providing a method for rearranging icons on a graphical user interface (GUI), wherein the method moves the most used icons to a position on the GUI, specifically, closest to the "start" icon of the computer system, based on a determined amount of use. In a first preferred embodiment, the amount of use of each icon is automatically determined by a processor that tracks the number of times each icon is selected or how much memory has been allocated to the individual processes associated with each icon over a period of time (e.g., day, week, month, etc.). In another embodiment, the user can choose to manually enter which icons are used most often using any of a number of ordering and/or ranking systems known to those skilled in the art.

The mobile application may first determine how many icons to display on the screen based on the size and dimensions of the mobile application's screen the icons may have a minimum width and height dimensions which are determined based on how large icons need to be so that users can easily tap on them. For example, if an icon is too short or too narrow, a user may have a difficult time tapping the desired icon and may instead tap an adjacent icon or empty space, thereby resulting in undesired behavior that may frustrate users. As an example, FIG. 5 shows a 2×2 icon grid. Additionally, the grantor dashboard may display asset, benefit, and/or budget information such as pie charts described in greater detail hereinabove. For example, the 2×2 icon grid may be arranged so that the most commonly used categories from the menu list described hereinabove are displayed and the others are accessible via a pop-up menu. For example, for the grantor, the icons displayed may be for the care plan, document vault, providers, and family/friends. For a beneficiary, the displayed icons may be for request money, request services, emergency, and medical & service providers. Note that emergency services may be a required icon for the beneficiary's icon grid. The center button—which may simply be a circular button interposed in the middle of a grid of icons—may be the most highly used or most important icon, owing to its central location and more prominent presentation. For example, clicking on the central icon may surface to the user a chat window with a care coordinator to make requests or follow up with previous requests.

The mobile application may be used to submit requests such as those described above. For example, a beneficiary may request transportation that uses location sensors of the mobile device. A beneficiary may request transportation from his or her current location to another location (e.g., arranging transportation to go home from the airport or another location). The location information can also be relayed to friends/family and/or emergency services.

The mobile application may implement similar to dashboards such as those described hereinabove. For example, FIG. 6 illustrates a finances dashboard 600 implemented in the context of a mobile device. The mobile device may present asset, benefits, and budget information, such as pie charts and percentage breakdowns thereof. Additionally, the mobile application may support swipe gestures so that swiping left or right results in the application switching between asset, benefit, and budget tabs.

Furthermore, a floating button may be present at the bottom of each screen except for the dashboard that includes two buttons. The first button may be a "home" button that brings the user back to the dashboard. The second button may be a chat icon (e.g., or any other suitable icon as described and/or selected in connection with the dashboard).

Care Coordination

As set forth in greater detail below, an aspect of a service platform in accordance with various embodiments is providing care coordinators a platform to provide planning, concierge, and fiduciary services. A care coordinator may access the service platform backend using privileged credentials and may have access to a care coordinator dashboard. The service platform backend may be integrated to other services such as ZENDESK™ support platform that clients use to submit requests and care coordinators can use to review requests and communicate with clients regarding the status of the request.

A care coordinator may have access to a menu list that can be used to navigate to multiple dashboards, which may be organized by: beneficiary accounts; users; approved vendors; reports; forms; ZENDESK™; care plan; harvest; and more. The beneficiary accounts page may include an alphabetized list of beneficiary accounts which can be searched and reviewed by the care coordinator. The list may include additional information about the beneficiary, such as age, gender, plan type, location, and an overview of the beneficiary's key needs, such as a list of their disabilities. The list may, in some cases, be sorted based on any suitable field. Clicking on a beneficiary's list item may navigate to that beneficiary's details screen.

FIG. 7 illustrates a detailed view 700 of a beneficiary account from the perspective of a care coordinator. The beneficiary account page may display an activity feed of the most recent requests that the beneficiary has made as well as communications between the care coordinator and the benefactor and/or beneficiary in a conversation view format. Upcoming service requests and/or money requests made through a customer support platform such as ZENDESK™ may also be displayed in the beneficiary account page.

A beneficiary account page may include an overview of information about the beneficiary, such as age, gender, date of birth, contact information, and more. The page may display information organized into multiple tabs such as an overview, info, finances, account users, and documents which the care coordinator can tab between for ease of access. The overview tab may include an overview of the beneficiary's abilities which is displayed as a radar graph using data provided through questionnaire answers. The info tab may display more detailed information about the beneficiary's account information, which may also be modified in this view. The finances tabs may include detailed financial information such as the information described in the finance's dashboard hereinabove. The finances tab may include a listing of assets among several sources, some of which are under the control of the service platform and which can be distributed by a care coordinator to a beneficiary. In various embodiments, funds are transferred from a trust account to an escrow account of the service platform that the beneficiary does not have direct access to. When the beneficiary needs money, a transfer is made from the escrow account to an account at least partially controlled by the beneficiary, such as a checking account jointly owned by the beneficiary, in at least one embodiment.

An account users tab may be accessible by the care coordinator to review requested changes to user permissions, requests to add users, and so on. These requests may also be surfaced in the activity feed. A care coordinator can review the permission update requests and process them accordingly. A documents tab may provide the care coordinator a view of the documents stored in the beneficiary's document vault which can include digital versions of one or documents such as passport data; personal tax returns; birth certificate; social security information; diploma and/or certification information; personal health information; and legal documents such as wills, trusts, living will or DNR/DNI documents; and more. Selecting a document may display the document details in a modal window that provides additional information about the document such as what type of document it is (e.g., tax return, medical reports, etc.) and may show which users have read and/or write access to the document. The providers tab may include the list of medical and/or professional providers and may include GUI elements that allow the care coordinator to add, remove, or modify providers. The governing trust document tab may provide legal users access to the governing trust document which details the specifics of the trust and its writers/associates. Users may be able to view and/or download the governing trust document.

A users dashboard may be accessible via a menu list by privileged users such as administrators of the service platform. This users dashboard may display the different users that act as care coordinators, supervisors, and administrators. Different users may have different permissions, such as access to read or write finances, management, and care plan information of beneficiary accounts.

The approved vendors dashboard may include a list of vendors which are pre-approved and can be used by various beneficiaries of the service platform. In some cases, when a beneficiary requests a service, a care coordinator can select an appropriate approved vendor and use that vendor to fulfill the service. If no approved vendor is suitable for fulfilling the request, then a care coordinator may need to take additional steps to find another provider not on the list.

Questionnaire and Decision Logic

As set forth in greater detail below, an aspect of a service platform in accordance with various embodiments is generating and organizing questionnaire questions and answers. As discussed elsewhere, a grantor or benefactor may, upon registration, be prompted with a sequence of questions relating to one or more aspects of the beneficiary's care, such as questions relating to medical, psychological, daily living, asset management, budget, general information, and more. Various types of questions are described in greater detail hereinbelow. Logic branching is described in greater detail herein below as well. There exist traditional questionnaires which ask all users a sequence of questions without regard to what the answer to a previous question was. For example, traditional questionnaires may have a question that asks a person for his gender, and then later ask whether he does or does not have a medical history of a series of diseases which includes ovarian cancer. Such a sequence of questions is inappropriate, at least because knowledge that a person's gender is male means that ovarian cancer is not a possible diagnosis. While this is a simple example, there are other types of logic branching which are used to first determine an area of need for a beneficiary and then ask subsequent questions around that area of need to better understand what the specific needs are and what medical or professional services are needed.

A first type of question that may be included in a questionnaire may be a multiple-choice type question. A multiple-choice question may present to a user a series of two or more choices to select from. In some cases, the user is only allowed to select one choice, in some cases, the user is allowed to select multiple choices. As an example of the former, the question may relate to a multiple choice question asking how long the grantor has known the beneficiary with non-overlapping time periods (e.g., 0-5 years, 6-10 years, 11-20 years, 20+ years). As an example of the latter, the question may relate to the types of accounts the user has where the accounts may be any combination of checking, savings, retirement, and trust accounts. In some cases, the user is able to add their own entry, such as in the case where the user has a different type of account from those listed in the checking, savings, retirement, and trust accounts.

A second type of question that may be included in a questionnaire may be a short answer question in which the user is prompted to provide a short text or numeric answer to a prompted question. For example, a short answer question may prompt a grantor to provide the total amount of money that he or she has control over.

A third type of question that may be included in a questionnaire may be an upload question. An upload question may include a text description of a request for the user to upload a file, for example, a registrant may be prompted to upload a spreadsheet with previous spending for the benefactor which can be used to generate budget and/or benefit items.

A fourth type of question that may be included in a questionnaire may be a form question. A form question may refer to a question that has a plurality of categories of which at least some require the user to submit a response. For example, a form question may prompt the user to provide what the monthly budget is for multiple categories of spending such as rent, utilities, transportation, food, etc.

A fifth type of question that may be included in a questionnaire may be an appointments question. The appointments questions may be a question in which the user specifies a monthly, weekly, or daily schedule. For example, the user may select a calendar entry of which monthly appointments/activities the grantor has or what weekly appointments the grantor has.

A sixth type of question that may be included in a questionnaire may be a property assets question for the user to provide details for real estate properties owned by the user, which may include a file upload option. A seventh question that may be included in a questionnaire may be a smiley face, in which a user selects an emoticon face that corresponds to the user's sentiment when presented with a question—for example, a user may be asked how the beneficiary feels about money in general by selecting a range of emoticon from an angry face to a happy face. An eighth type of question that may be included in a questionnaire may be a sliding scale in which a user selects, on a customizable range (e.g., 1-5 or 1-10) an answer. For example, a user may select on a scale of 1-10 how capable the beneficiary is of managing his or her own finances.

A radar question may be a type of question included in a questionnaire in which a user provides an answer to a question that forms a leg of a radar graph or spider graph. For example, a user may be prompted through a series of questions that form the different legs of a radar graph that includes the following: ability to express needs; emotional stability; physical ability; financial ability; and honesty/truth.

In some cases, a user is prompted to synchronize an external account to the service platform. An external account may refer to an account hosted or managed by another entity, such as a banking organization. Syncing the external account to the service platform can involve the user providing credentials (e.g., username, password, PIN, etc.) to the external account. Once the external account is synced, financial, medical, etc. data may be pulled directly from the external account and may be synced periodically to keep balances and other information fresh.

Figure 8:
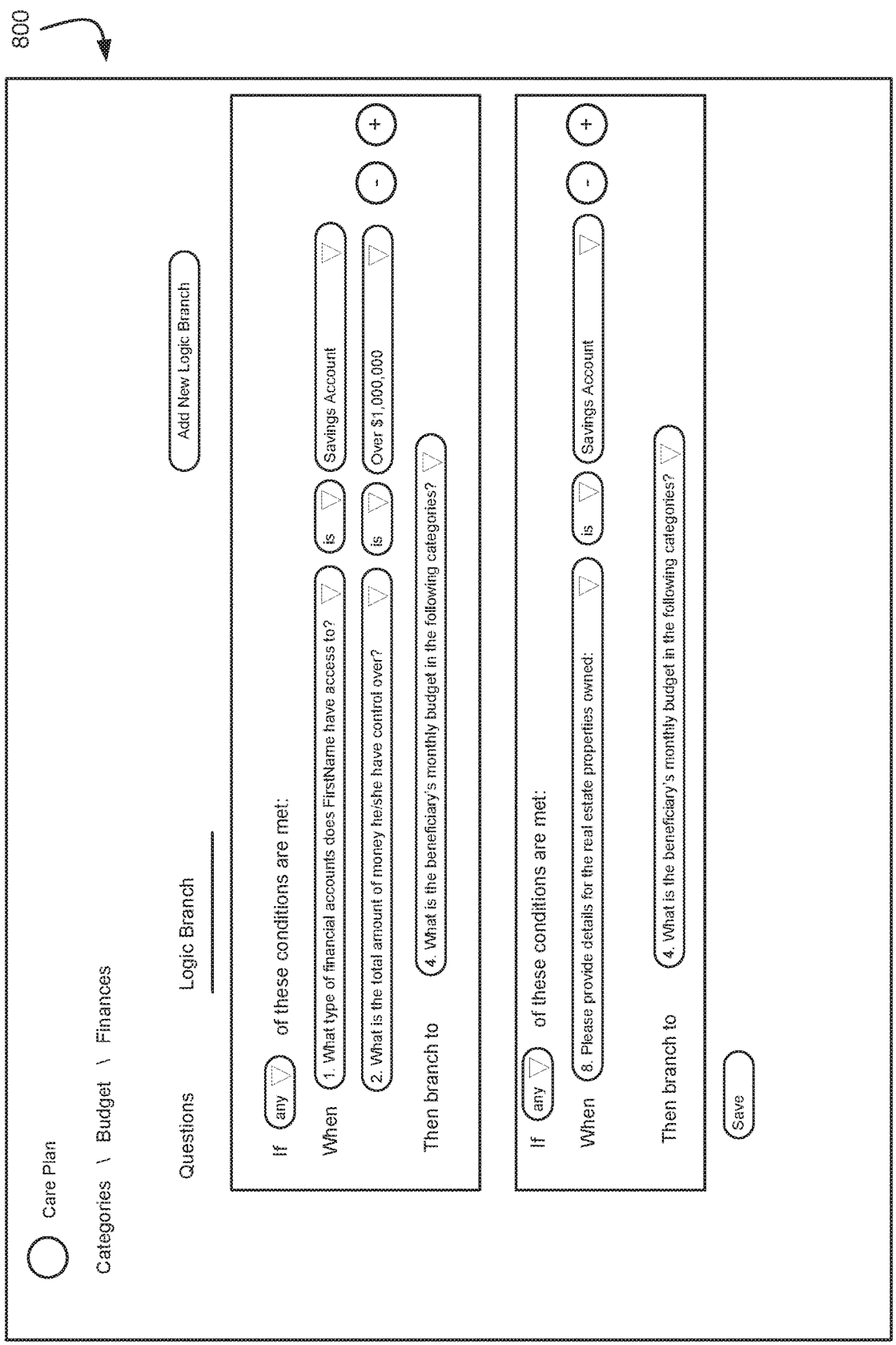
FIG. 8 illustrates a diagram of logic branching, in accordance with at least one embodiment.

FIG. 8 illustrates a diagram 800 of a logic branch which may be used to determine the sequence of questions that are presented to a user in a questionnaire. Decision logic may refer to a set of rules for determining a sequence of questionnaire questions to present to a user which relies upon previous answers. For example, an administrator can create conditional questions that are displayed only in the event that a previous question has been filled in with a specific answer that meets one or more conditions. The administrator may start with one condition which must be satisfied for a question to be presented, and may have the option of including additional conditions which can be linked to other conditions by binary logic (e.g., AND/OR logic). Each condition may be a logical expression which can be resolved to true false, or sometimes not enough information (e.g., another question which the present one relies upon has not yet been answered). For example, a user may be prompted with a first question asking what types of financial accounts the user has access to and a second question asking what the total amount of money the user has. If the first question was answered such that the user has access to a savings account (answer to first question) and the total amount of money is over $1,000,000 (answer to second question), then the logic branch may indicate to branch to a fourth question (e.g., skipping a third question).

Figure 9:
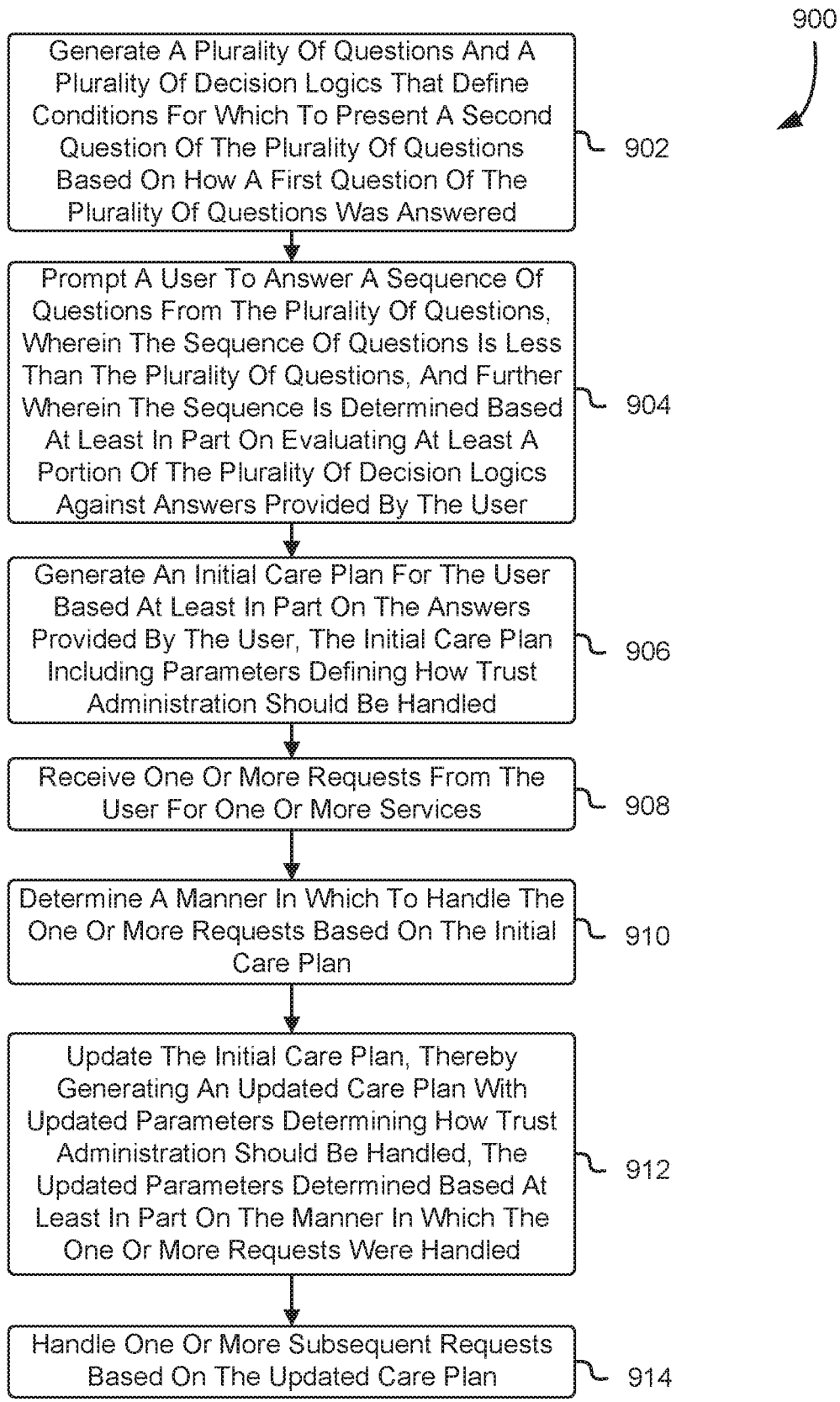
FIG. 9 shows an illustrative example of a process to develop a care plan in accordance with at least one embodiment.

FIG. 9 shows an illustrative example of a process 900 to develop a care plan in accordance with at least one embodiment. In at least one embodiment, some or all of the process 900 (or any other processes described herein, or variations and/or combinations thereof) is performed under the control of one or more computer systems configured with computer-executable instructions and may be implemented as code (e.g., computer-executable instructions, one or more computer programs, or one or more applications) executing collectively on one or more processors, by hardware, software, or combinations thereof. A process in accordance with FIG. 9 may be implemented in the context of FIGS. 1 and/or 10, and others, for example. The code, in at least one embodiment, is stored on a computer-readable storage medium in the form of a computer program including a plurality of computer-readable instructions executable by one or more processors. The computer-readable storage medium, in at least one embodiment, is a non-transitory computer-readable medium. In at least one embodiment, at least some of the computer-readable instructions usable to perform the process 900 are not stored solely using transitory signals (e.g., a propagating transient electric or electromagnetic transmission). A non-transitory computer-readable medium does not necessarily include non-transitory data storage circuitry (e.g., buffers, caches, and queues) within transceivers of transitory signals.

A user such as a grantor may initiate a registration process over the Internet using a web or mobile application. The user can be walked through a set of registration steps in which he or she provides biographical information about himself or herself, and is prompted to provide additional information about a beneficiary, who may be a second user that later signs up with a service platform. The service platform may be used to provide planning, concierge, and fiduciary services.

Either during or after registration, a user may be prompted with a sequence of questions that is determined using decision logic wherein answers to previous questions may affect which subsequent questions may be asked. A repository of thousands of questions (or more) relating to different aspects of a beneficiary's life may be available in the service platform, but only select questions may be asked based on the needs that the user describes. For example, a user may be prompted with one question that asks about how comfortable the beneficiary is with his or her daily mobility on a scale of 1-5 with 1 being mostly uncomfortable and 5 being mostly comfortable. If the user answers a 5, then questions relating to certain types of mobility-related disabilities may be omitted. However, if the user answers a 1, then the decision logic may cause additional questions to be asked relating to mobility, such as questions relating to whether the user has any illnesses or ailments that affect his or her mobility, whether he or she has had any surgeries, how long he or she has had difficulties with disabilities, whether he or she has any in-home care givers, and what types of services or mitigations that he or she may have in place to assist with the mobility challenges. Accordingly, the decision logic may be used to determine parameters for a care plan that relate to mobility-assistance, such as preparing grocery delivery services to alleviate the challenges that the beneficiary may have in going to a supermarket to buy groceries.

Questionnaire answers may be provided by the beneficiary or from another party such as the grantor or family members, medical professionals, financial professionals, legal professionals, and more. For example, a beneficiary that has recently suffered a surgery that impacts his or her mobility may have physical therapy sessions scheduled through the care coordinator, who may update the beneficiary's mobility from a 5 to a 1 as a result of the surgery. As a result of this change, the care plan may also provide for grocery delivery as an option which the beneficiary or grantor may choose either to accept or decline. In some cases, these services may be provided automatically based on the updated care data. In some cases, machine learning or artificial intelligence techniques may be applied to make suggestions for types of care that can be provided to a beneficiary when his or her care data changes.

In at least some embodiments, the process 900 includes generating 902 a plurality of questions and a plurality of decision logics that define conditions for which to present a second question of the plurality of questions based on how a first question of the plurality of questions was answered. A decision logic may be a set of conditions that are used to determine whether a particular question should be presented and/or what the next question to present is. For example, if a question relates to the beneficiary's ability to manage his or her own finances and the answer indicates that he or she is fully capable of managing his or her own finances, than questions relating to helping the beneficiary manage his or her finances may be skipped. The plurality of questions may have a default ordering (e.g., 1, 2, 3, etc.) and the decision logic may be used to skip or reorder certain questions. A plurality of questions, or a portion thereof, may be included in a single questionnaire, and a user may be prompted to answer several different questionnaires that relate to the medical, psychological, dialing living, asset management, budget, general information of the user, and more.

In at least some embodiments, the process 900 includes prompting 904 a user to answer a sequence of questions from the plurality of questions, wherein the sequence of questions is less than the plurality of questions, and further wherein the sequence is determined based at least in part on evaluating at least a portion of the plurality of decision logics against answers provided by the user. A user such as a grantor or beneficiary may be prompted to answer a series of questions about the beneficiary. The sequence of questions that the user answers may be fewer than the total number of questions that are available in a questionnaire, perhaps because decision logic caused certain questions to be skipped in response to an answer of a question that indicates certain questions are not relevant or are not as important to the care plan.

In at least some embodiments, the process 900 includes generating 906 an initial care plan for the user based at least in part on the answers provided by the user, the initial care plan including parameters defining how trust administration is to be handled. A care plan may refer to the parameters of a trust, such as the terms by which the trust is administered. A trust may be programmatically generated using wild cards and programmatic tools to take a template, remove unnecessary sections, and automatically fill in certain fields with values from the user's biographical information.

In at least some embodiments, the process 900 includes receiving 908 one or more requests from the user for one or more services. A request may be made by the user over a web application or mobile application. For example, a user may submit an in-app chat request for in-kind or monetary benefits. Communications infrastructure, such as those described in connection with FIG. 1, may be used to make requests. In some case, a ticketing platform such as ZENDESK™ support platform used to generate tickets, which a care coordinator may pick up and handle based on the parameters of the care plan.

In at least some embodiments, the process 900 includes determining 910 a manner in which to handle the one or more requests based on the initial care plan. The manner in which to handle the requests may involve setting up an appointment using an approved vendor, scheduling a periodic visit for a social worker, checking whether a request for money disbursements impacts the beneficiary's eligibility for government benefits, and so on. Determining a manner in which to handle a request may involve a care coordinator picking up and reviewing a request ticket from a ticketing platform such as ZENDESK™ support platform.

In at least some embodiments, the process 900 includes updating 912 the initial care plan, thereby generating an updated care plan with updated parameters determining how trust administration is to be handled, the updated parameters determined based at least in part on the manner in which the one or more requests were handled. For example, a request may involve a doctor's visit in which the user visits a doctor. A care coordinator may follow up with the request and ask the doctor for results of the visit. Those results may include a diagnosis, evaluation of an existing condition, and more. It should be noted that in some cases, the care coordinator acts on behalf of the service platform which has received a medical release that allows representatives of the service platform to request medical information of a beneficiary, in accordance with any and all applicable laws and regulations. These results may be used to update the parameters of the care plan—for example, if a beneficiary has a chronic condition, the care coordinator may monitor trends to determine whether the condition is improving or getting worse and recommend adjusting parameters to the care plan based on how the condition changes. Once the care plan has been updated, a system performing process 900 may continue by handling 914 one or more subsequent requests based on the updated care plan and updated parameters.

In some cases, the sequence of questions prompted to the user relate to the medical, psychological, dialing living, asset management, budget, and general information of the user. In some cases, process 900 further includes scheduling one or more disbursements to the user on a periodic schedule based on the parameters of the trust administration. The request described above may be a medical request and the manner in which to handle the one or more requests includes scheduling an appointment for the medical request and process 900 may further includes receiving additional care data as a result of the medical request, wherein the additional care data is relevant to how the trust administration is to be handled. The user of process 900 may be a special needs beneficiary of a non-discretionary trust.

Figure 10:
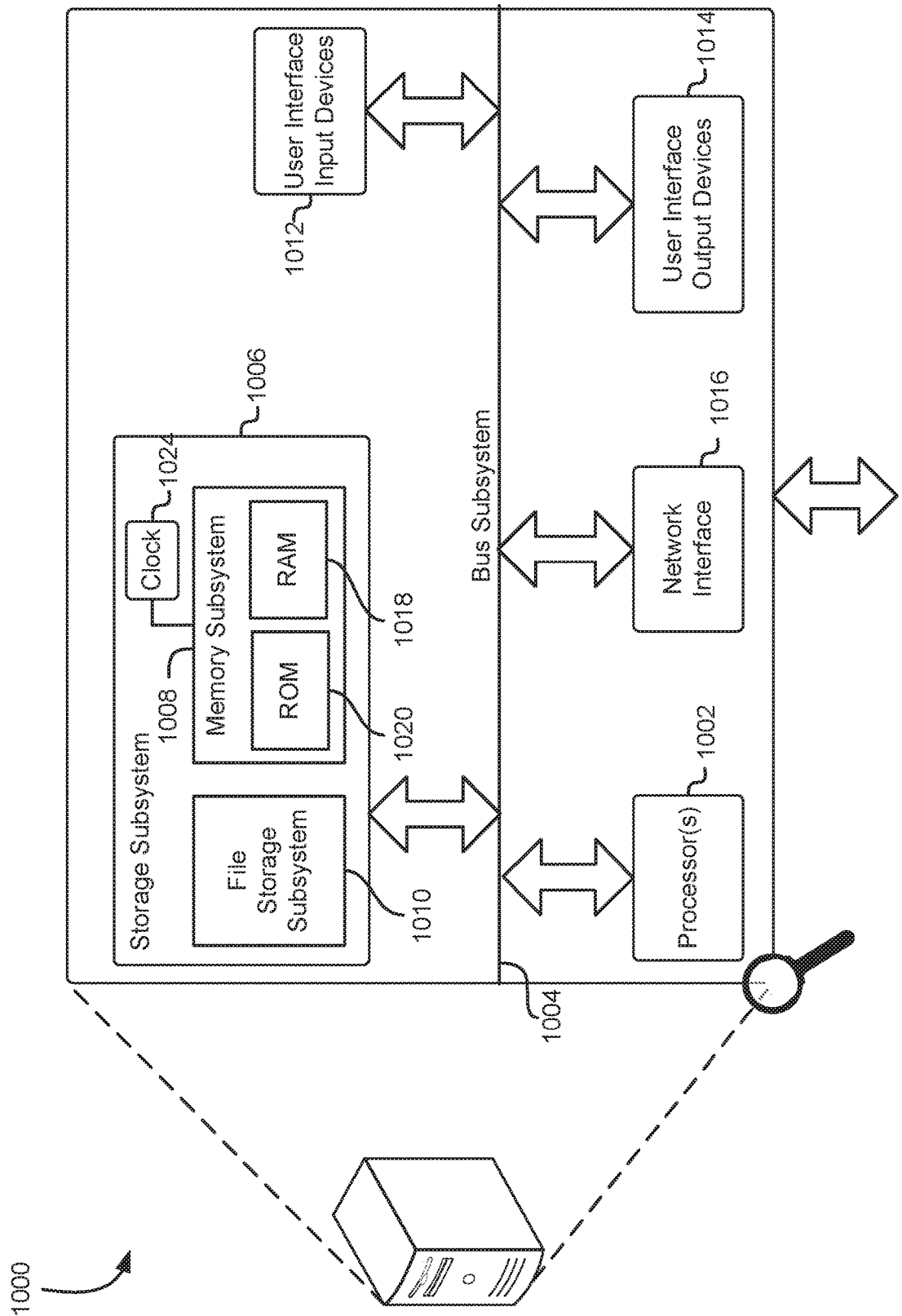
FIG. 10 illustrates an environment in which various embodiments can be implemented.

FIG. 10 is an illustrative, simplified block diagram of a computing device 1000 that can be used to practice at least one embodiment of the present disclosure. In various embodiments, the computing device 1000 may be used to implement any of the systems illustrated and described above. For example, the computing device 1000 may be configured for use as a data server, a web server, a portable computing device, a personal computer, or any electronic computing device. As shown in FIG. 10, the computing device 1000 may include one or more processors 1002 that, in embodiments, communicate with and are operatively coupled to a number of peripheral subsystems via a bus subsystem. In some embodiments, these peripheral subsystems include a storage subsystem 1006, comprising a memory subsystem 1008 and a file/disk storage subsystem 1010, one or more user interface input devices 1012, one or more user interface output devices 1014, and a network interface subsystem 1016. Such storage subsystem 1006 may be used for temporary or long-term storage of information.

In some embodiments, the bus subsystem 1004 may provide a mechanism for enabling the various components and subsystems of computing device 1000 to communicate with each other as intended. Although the bus subsystem 1004 is shown schematically as a single bus, alternative embodiments of the bus subsystem utilize multiple buses. The network interface subsystem 1016 may provide an interface to other computing devices and networks. The network interface subsystem 1016 may serve as an interface for receiving data from and transmitting data to other systems from the computing device 1000. In some embodiments, the bus subsystem 1004 is utilized for communicating data such as details, search terms, and so on.

In some embodiments, the user interface input devices 1012 includes one or more user input devices such as a keyboard; pointing devices such as an integrated mouse, trackball, touchpad, or graphics tablet; a scanner; a barcode scanner; a touch screen incorporated into the display; audio input devices such as voice recognition systems, microphones; and other types of input devices. In general, use of the term "input device" is intended to include all possible types of devices and mechanisms for inputting information to the computing device 1000. In some embodiments, the one or more user interface output devices 1014 include a display subsystem, a printer, or non-visual displays such as audio output devices, etc. In some embodiments, the display subsystem includes a cathode ray tube (CRT), a flat-panel device such as a liquid crystal display (LCD), light emitting diode (LED) display, or a projection or other display device. In general, use of the term "output device" is intended to include all possible types of devices and mechanisms for outputting information from the computing device 1000. The one or more user interface output devices 1014 can be used, for example, to present user interfaces to facilitate user interaction with applications performing processes described and variations therein, when such interaction may be appropriate.

In some embodiments, the storage subsystem 1006 provides a computer-readable storage medium for storing the basic programming and data constructs that provide the functionality of at least one embodiment of the present disclosure. The applications (programs, code modules, instructions), when executed by one or more processors in some embodiments, provide the functionality of one or more embodiments of the present disclosure and, in embodiments, are stored in the storage subsystem 1006. These application modules or instructions can be executed by the one or more processors 1002. In various embodiments, the storage subsystem 1006 additionally provides a repository for storing data used in accordance with the present disclosure. In some embodiments, the storage subsystem 1006 includes a memory subsystem 1008 and a file/disk storage subsystem 1010.

In embodiments, the memory subsystem 1008 includes a number of memories, such as a main random access memory (RAM) 1018 for storage of instructions and data during program execution and/or a read only memory (ROM) 1020, in which fixed instructions can be stored. In some embodiments, the file/disk storage subsystem 1010 provides a non-transitory persistent (non-volatile) storage for program and data files and can include a hard disk drive, a floppy disk drive along with associated removable media, a Compact Disk Read Only Memory (CD-ROM) drive, an optical drive, removable media cartridges, or other like storage media.

In some embodiments, the computing device 1000 includes at least one local clock 1024. The at least one local clock 1024, in some embodiments, is a counter that represents the number of ticks that have transpired from a particular starting date and, in some embodiments, is located integrally within the computing device 1000. In various embodiments, the at least one local clock 1024 is used to synchronize data transfers in the processors for the computing device 1000 and the subsystems included therein at specific clock pulses and can be used to coordinate synchronous operations between the computing device 1000 and other systems in a data center. In another embodiment, the local clock is a programmable interval timer.

The computing device 1000 could be of any of a variety of types, including a portable computer device, tablet computer, a workstation, or any other device described below. Additionally, the computing device 1000 can include another device that, in some embodiments, can be connected to the computing device 1000 through one or more ports (e.g., USB, a headphone jack, Lightning connector, etc.). In embodiments, such a device includes a port that accepts a fiber-optic connector. Accordingly, in some embodiments, this device is that converts optical signals to electrical signals that are transmitted through the port connecting the device to the computing device 1000 for processing. Due to the ever-changing nature of computers and networks, the description of the computing device 1000 depicted in FIG. 10 is intended only as a specific example for purposes of illustrating the preferred embodiment of the device. Many other configurations having more or fewer components than the system depicted in FIG. 10 are possible.

The specification and drawings are, accordingly, to be regarded in an illustrative rather than a restrictive sense. However, it will be evident that various modifications and changes may be made thereunto without departing from the scope of the invention as set forth in the claims. Likewise, other variations are within the scope of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed but, on the contrary, the intention is to cover all modifications, alternative constructions and equivalents falling within the scope of the invention, as defined in the appended claims.

The use of the terms "a" and "an" and "the" and similar referents in the context of describing the disclosed embodiments (especially in the context of the following claims) is to be construed to cover both the singular and the plural, unless otherwise indicated or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values in the present disclosure are merely intended to serve as a shorthand method of referring individually to each separate value falling within the range unless otherwise indicated and each separate value is incorporated into the specification as if it were individually recited. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Conjunctive language, such as phrases of the form "at least one of A, B, and C," or "at least one of A, B and C," unless specifically stated otherwise or otherwise clearly contradicted by context, is otherwise understood with the context as used in general to present that an item, term, etc., could be either A or B or C, or any nonempty subset of the set of A and B and C. For instance, in the illustrative example of a set having three members, the conjunctive phrases "at least one of A, B, and C" and "at least one of A, B, and C" refer to any of the following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present. Further, unless stated otherwise or otherwise clear from context, the phrase "based on" means "based at least in part on" and not "based solely on."

Operations of processes described can be performed in any suitable order unless otherwise indicated or otherwise clearly contradicted by context. Processes described (or variations and/or combinations thereof) can be performed under the control of one or more computer systems configured with executable instructions and can be implemented as code (e.g., executable instructions, one or more computer programs or one or more applications) executing collectively on one or more processors, by hardware or combinations thereof. In some embodiments, the code can be stored on a computer-readable storage medium, for example, in the form of a computer program comprising a plurality of instructions executable by one or more processors. In some embodiments, the computer-readable storage medium is non-transitory.

The use of any and all examples, or exemplary language (e.g., "such as") provided, is intended merely to better illuminate embodiments of the invention and does not pose a limitation on the scope of the invention unless otherwise claimed. No language in the specification should be construed as indicating any non-claimed element as essential to the practice of the invention.

Embodiments of this disclosure are described, including the best mode known to the inventors for carrying out the invention. Variations of those embodiments will become apparent to those of ordinary skill in the art upon reading the foregoing description. The inventors expect skilled artisans to employ such variations as appropriate and the inventors intend for embodiments of the present disclosure to be practiced otherwise than as specifically described. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated or otherwise clearly contradicted by context.

All references, including publications, patent applications, and patents, cited are hereby incorporated by reference to the same extent as if each reference were individually and specifically indicated to be incorporated by reference and were set forth in its entirety.

What is claimed is:

1. A method, comprising:
    generating, using a care planning component of a service platform running on a highly available hosting environment, a plurality of questions and a plurality of decision logics, wherein a first decision logic of the plurality of decision logics specifies a first set of condition, further wherein each condition of the set of conditions specifies a question of the plurality of questions and a predetermined value, further wherein the first decision logic is associated with a different question of the plurality of questions, further wherein a determination of whether the different question should be presented to the user is made based on a comparison of a user's answer to the question and the predetermined value;
    prompting a user to answer a sequence of questions from the plurality of questions using a frontend application of the service platform that is connected to the care planning component, wherein the sequence of questions is less than the plurality of questions, and further wherein the sequence is determined based at least in part on evaluating at least a portion of the plurality of decision logics against answers provided by the user;
    generating, using the care planning component of the service platform, an initial care plan for the user based at least in part on the answers provided by the user, the initial care plan including parameters defining how trust administration is to be handled;
    receiving, via a customer support component of the service platform, a plurality of requests from the user for one or more services, wherein the customer support component is connected to the frontend application and supports one or more modalities of communication, further wherein the one or more modalities of communications includes:
        a ticketing platform that the user can directly submit requests to; and
        an in-app chat applet that facilitates communications between the user and a care coordinator, wherein the care coordinator also has access to submit additional requests to the ticketing platform, wherein at least one of the additional requests requires approval of the care coordinator to be processed;
    determining a manner in which to handle the plurality of requests based on the initial care plan, wherein at least a portion of the plurality of requests are aggregated based on a common characteristic and processed together;
    updating the initial care plan, thereby generating an updated care plan with updated parameters determining how the trust administration is to be handled, the updated parameters determined based at least in part on the manner in which the plurality of requests were handled; and
    handling one or more subsequent requests based on the updated care plan.

2. The method of claim 1, wherein the sequence of questions prompted to the user relate to the medical, psychological, dialing living, asset management, budget, and general information of the user.

3. The method of claim 1, further comprising scheduling one or more disbursements to the user on a periodic schedule based on the parameters of the trust administration.

4. The method of claim 3, wherein the one or more disbursements include in-kind disbursements.

5. The method of claim 1, wherein:
    a request is a medical request and the manner in which to handle the one or more requests includes scheduling an appointment for the medical request; and
    the method further includes receiving additional care data as a result of the medical request, wherein the additional care data is relevant to how the trust administration is to be handled.

6. The method of claim 1, wherein the user is a special needs beneficiary.

7. A system, comprising memory that stores a set of instructions which, as a result of execution by one or more processors, cause the system to:
    generate, using a care planning component of a service platform running on a highly available hosting environment, a plurality of questions and a plurality of decision logics wherein a first decision logic of the plurality of decision logics specifies a first set of condition, further wherein each condition of the set of conditions specifies a question of the plurality of questions and a predetermined value, further wherein the first decision logic is associated with a different question of the plurality of questions, further wherein a determination of whether the different question should be presented to the user is made based on a comparison of a user's answer to the question and the predetermined value;
    prompt a user to answer a sequence of questions from the plurality of questions using a frontend application of the service platform that is connected to the care planning component, wherein the sequence of questions is less than the plurality of questions, and further wherein the sequence is determined based at least in part on evaluating at least a portion of the plurality of decision logics against answers provided by the user;
    generate, using the care planning component of the service platform, an initial care plan for the user based at least in part on the answers provided by the user, the initial care plan including parameters defining how trust administration is to be handled;
    receive, via a customer support component of the service platform, a plurality of requests from the user for one or more services, wherein the customer support component is connected to the frontend application and supports one or more modalities of communication, further wherein the one or more modalities of communications includes:
        a ticketing platform that the user can directly submit requests to; and an in-app chat applet that facilitates communications between the user and a care coordinator, wherein the care coordinator also has access to submit additional requests to the ticketing platform, wherein at least one of the additional requests requires approval of the care coordinator to be processed;

determine a manner in which to handle the plurality of requests based on the initial care plan, wherein at least a portion of the plurality of requests are aggregated based on a common characteristic and processed together;

update the initial care plan, thereby generating an updated care plan with updated parameters determining how the trust administration is to be handled, the updated parameters determined based at least in part on the manner in which the plurality of requests were handled; and handle one or more subsequent requests based on the updated care plan.

8. The system of claim 7, wherein the sequence of questions prompted to the user relate to the medical, psychological, dialing living, asset management, budget, and general information of the user.

9. The system of claim 7, wherein the instructions include further instructions that, as a result of execution by the one or more processors, further cause the system to schedule one or more disbursements to the user on a periodic schedule based on the parameters of the trust administration.

10. The system of claim 9, wherein the one or more disbursements include in-kind disbursements.

11. The system of claim 7, wherein:
a request is a medical request and the manner in which to handle the one or more requests includes scheduling an appointment for the medical request; and
the instructions include further instructions that, as a result of execution by the one or more processors, cause the system to receive additional care data as a result of the medical request, wherein the additional care data is relevant to how the trust administration is to be handled.

12. The system of claim 7, wherein the user is a special needs beneficiary.

13. A non-transitory computer-readable storage medium storing executable instructions that, as a result of execution by one or more processors of a computer system, cause the computer system to:
generate, using a care planning component of a service platform running on a highly available hosting environment, a plurality of questions and a plurality of decision logics wherein a first decision logic of the plurality of decision logics specifies a first set of condition, further wherein each condition of the set of conditions specifies a question of the plurality of questions and a predetermined value, further wherein the first decision logic is associated with a different question of the plurality of questions, further wherein a determination of whether the different question should be presented to the user is made based on a comparison of a user's answer to the question and the predetermined value;
prompt a user to answer a sequence of questions from the plurality of questions using a frontend application of the service platform that is connected to the care planning component, wherein the sequence of questions is less than the plurality of questions, and further wherein the sequence is determined based at least in part on evaluating at least a portion of the plurality of decision logics against answers provided by the user;
generate an initial care plan for the user based at least in part on the answers provided by the user, the initial care plan including parameters defining how trust administration is to be handled;
receive, via a customer support component of the service platform, a plurality of requests from the user for one or more services, wherein the customer support component is connected to the frontend application and supports one or more modalities of communication, further wherein the one or more modalities of communications includes:
a ticketing platform that the user can directly submit requests to; and
an in-app chat applet that facilitates communications between the user and a care coordinator, wherein the care coordinator also has access to submit additional requests to the ticketing platform, wherein at least one of the additional requests requires approval of the care coordinator to be processed;
determine a manner in which to handle the plurality of requests based on the initial care plan, wherein at least a portion of the plurality of requests are aggregated based on a common characteristic and processed together;
update the initial care plan, thereby generating an updated care plan with updated parameters determining how the trust administration is to be handled, the updated parameters determined based at least in part on the manner in which the plurality of requests were handled; and
handle one or more subsequent requests based on the updated care plan.

14. The non-transitory computer-readable storage medium of claim 13, wherein the sequence of questions prompted to the user relate to the medical, psychological, dialing living, asset management, budget, and general information of the user.

15. The non-transitory computer-readable storage medium of claim 13, wherein the instructions include further instructions that, as a result of execution by the one or more processors, cause the computer system to schedule one or more disbursements to the user on a periodic schedule based on the parameters of the trust administration.

16. The non-transitory computer-readable storage medium of claim 15, wherein the one or more disbursements include in-kind disbursements.

17. The non-transitory computer-readable storage medium of claim 13, wherein:
a request is a medical request and the manner in which to handle the one or more requests includes scheduling an appointment for the medical request; and
the instructions include further instructions that, as a result of execution by the one or more processors, cause the computer system to receive additional care data as a result of the medical request, wherein the additional care data is relevant to how the trust administration is to be handled.

* * * * *